(12) United States Patent
Brocia et al.

(10) Patent No.: US 7,618,784 B2
(45) Date of Patent: Nov. 17, 2009

(54) ASSAY FOR PHOSPHOLIPID TRANSFER PROTEIN (PLTP) ACTIVITY

(75) Inventors: Robert W. Brocia, Bronxville, NY (US); Xian-Cheng Jiang, Fort Lee, NJ (US)

(73) Assignee: Roar Holding LLC, New York, NY (US)

(*) Notice: Subject to any disclaimer, the term of this patent is extended or adjusted under 35 U.S.C. 154(b) by 0 days.

(21) Appl. No.: 10/279,787

(22) Filed: Oct. 23, 2002

(65) Prior Publication Data

US 2003/0235859 A1 Dec. 25, 2003

Related U.S. Application Data

(60) Provisional application No. 60/348,722, filed on Oct. 23, 2001.

(51) Int. Cl.
*G01N 33/53* (2006.01)

(52) U.S. Cl. ............... 435/7.1; 435/4; 435/7.2; 435/7.21; 435/7.72; 435/40.5; 436/501; 436/506; 436/518; 436/534; 436/535; 424/9.1; 424/9.6; 424/489

(58) Field of Classification Search ............ 435/4, 435/7.1, 7.2, 7.72, 40.5–40.51, 174, DIG. 1–DIG. 51; 436/56, 71, 164, 172, 800, 524, 535, 13, 436/74, 79, 105, 805; 424/450, 489, 502, 424/477, 9.6, 9.61
See application file for complete search history.

(56) References Cited

U.S. PATENT DOCUMENTS

| | | | | |
|---|---|---|---|---|
| 3,635,470 | A * | 1/1972 | McMillan | 472/51 |
| 4,394,448 | A | 7/1983 | Szoka, Jr. et al. | 435/172 |
| 5,225,329 | A * | 7/1993 | Marks | 435/7.9 |
| 5,459,567 | A * | 10/1995 | Brocia | 356/318 |
| 5,585,235 | A * | 12/1996 | Brocia | 435/4 |
| 5,610,071 | A | 3/1997 | Day et al. | 435/7.1 |
| 5,618,683 | A * | 4/1997 | Brocia et al. | 435/11 |
| 5,622,843 | A | 4/1997 | Day et al. | 435/69.6 |
| 5,641,508 | A | 6/1997 | Li et al. | |
| 5,770,355 | A * | 6/1998 | Brocia | 435/4 |
| 5,776,470 | A * | 7/1998 | Schmidt | 424/401 |
| 5,888,742 | A * | 3/1999 | Lal et al. | 435/6 |
| 6,063,767 | A * | 5/2000 | Lal et al. | 514/12 |
| 6,174,693 | B1 * | 1/2001 | Brocia | 435/7.4 |
| 6,465,007 | B1 | 10/2002 | Eastman et al. | 424/450 |
| 6,974,676 | B1 | 12/2005 | Brocia | |
| 7,279,297 | B2 | 10/2007 | Brocia | |
| 2002/0187997 | A1 * | 12/2002 | Chin | 514/283 |
| 2003/0119730 | A1 * | 6/2003 | Lal et al. | 514/12 |
| 2005/0082091 | A1 * | 4/2005 | Kingsley | 175/207 |

OTHER PUBLICATIONS

Yu B & Wright SD. Catalytic Properties of Lipopolysaccharide (LPS) Binding Protein. J. Biol. Chem. 1996;271:4100-4105.*
Bisgaier CL et al. Use of fluorescent cholesteryl ester microemulsions in cholesteryl ester transfer protein assays. J. Lipid Res. 1993;34:1625-1634.*
Nichols JW. Binding of Fluorescent-labeled Phosphatidylcholine to Rat Liver Nonspecific Lipid Transfer Protein. J. Biol. Chem. 1987;262:14172-14177.*
Somerharju P. et al. A new fluorimetric method to measure protein-catalyzed phospholipid transfer using 1-acyl-2-parinaroylphosphatidylcholine. Biochim. Biophys. Acta. 1981;649:521-528.*
Chattopadhyay A. Chemistry and biology of N-(7-nitrobenz-2-oxa-1,3-diazol-4-yl)-labeled lipids: fluorescent probes of biological and model membranes. Chem. Phys. Lipids. 1990;53:1-15.*
Voziyan, PA. et al. Importance of phospholipid in the folding and conformation of phosphatidylinositol transfer protein: Comparison of apo and holo species. Biochemistry. 1997;36:10082-10088.*
Grundy, S.M. Richard Havel, Howard Eder, and the evolution of lipoprotein analysis. J. Clin. Invest. 2004;114:1034-1037.*
Havel, R.J. et al. The distribution and chemical composition of ultracentrifugally separated lipoproteins in human serum. J. Clin. Invest. 1955;34:1345-1353.*
International Search Report, mailed on Oct. 27, 2003, for PCT patent application No. PCT/US02/34041, filed on Oct. 23, 2002, 4 pages.
Hailman et al., J. Biol. Chem. (1996) 271:12172-12178.
Huuskonen et al., Biochem/Biophys. Acta (1996) 1303:207-214.
Lalanne et al., J. Lipid Res. (2001) 42:142-149.
Nichols, Seminars in Cell and Developmental Biology (2002) 13:190-184.
Oskolkova et al., Chem. Phys. Lipids (1999) 99:73-86.
Tall, An. Rev. Biochem. (1995) 64:235-237.
International Preliminary Examination Report for PCT/US02/34041, mailed on Jan. 31, 2005, 4 pages.
Supplementary European Search Report for EP 02 77 0661, mailed on Mar. 28, 2007, 3 pages.
Pussinen et al., Biochimica et Biophysica Acta (2001) 1533(2):153-163.

* cited by examiner

*Primary Examiner*—Lisa V Cook
(74) *Attorney, Agent, or Firm*—Morrison & Foerster LLP

(57) ABSTRACT

Improved methods for assaying the activity of phospholipid transfer protein (PLTP) enhance the signal-to-noise ratio by providing the substrate in donor particles with an aqueous core in the presence of suitable osmotic pressure.

21 Claims, 3 Drawing Sheets

Liposome / Donor Particle
↓ Osmolality ~ 2.7

← Label

→ PLTP →

Acceptor Emulsion

Disrupted Donor

ASSAY FOR PHOSPHOLIPID TRANSFER PROTEIN (PLTP) ACTIVITY

CROSS-REFERENCE TO RELATED APPLICATIONS

This application claims priority under 35 U.S.C. § 119(e) to provisional application 60/348,722 filed 23 Oct. 2001. The contents of this application are incorporated herein by reference.

TECHNICAL FIELD

The invention is directed to improved methods to assay for the activity of phospholipid transfer protein (PLTP). Such assays are useful in identifying compounds that inhibit PLTP activity and in assessing conditions related to abnormal PLTP activity.

BACKGROUND ART

PLTP is a 51 kD protein containing 476 amino acid residues found mostly in plasma, placenta and pancreas but also present in lung, kidney, heart, liver, skeletal muscle, small intestine and brain. The nucleotide sequence encoding this protein has been cloned and sequenced as disclosed in U.S. Pat. No. 5,610,019, the contents of which are incorporated herein by reference. The activity of this protein has been reviewed by Tall, in *An. Rev. Biochem.* (1995) 64:235-237. PLTP facilitates transfer of substrates which include phospholipids, diglycerides and vitamin E from donor unilamellar vessels or lipoproteins into HDL or other lipoproteins. It is also known that PLTP plays a role in HDL formation and in regulating the secretion of Apo-B containing lipoproteins. It also plays a role in atherosclerosis development. Cholesterol ester transfer protein (CETP) activity is also enhanced by PLTP.

With respect to assays for PLTP activity, the above-referenced '019 patent describes a heterogeneous assay where the acceptor is biotinylated HDL. In a study involving assessing the substrate specificity of PLTP, in particular in investigating whether PLTP would interact with LPS, Hailman, E., et al., *J. Biol. Chem.* (1996) 271:12172-12178 describe an assay in which LPS labeled with the fluorophore boron dipyrromethane difluoride (BODIPY) is transferred from self-associated micelles to various acceptors. The authors found that PLTP could mediate the exchange to HDL particles but not to CD14.

Oskolkova, O. V., et al., *Chem. Phys. Lipids* (1999) 99:73-86 employed pyrene conjugates of phospholipid-coupled thymidine to monitor, the spontaneous transfer of thymidine from vesicles to acceptors; high levels of spontaneous transfer were observed.

Pyrene was also used as a label by Huuskonen, J., et al., *Biochem/Biophys. Acta* (1996) 1303:207-214. These authors studied the specificity of the enzyme using pyrene-labeled phospholipids from quenched donor phospholipid vessels to $HDL_3$ particles.

Lalanne, F., et al., *J. Lipid Res.* (2001) 42:142-149, in studying the modulation of transfer of phospholipids by diacylglycerols also employed pyrene-labeled phosphatidylcholine and measured transfer from various types of vesicles to HDL.

While pyrene is often referred to as self-quenching, this is not in fact the case. Pyrene has a monomer/excimer emission profile whereby at low concentrations the monomer fluoresces at 390 nm but at higher concentrations the emission shifts to 470 nm. The ratio of 390/470 intensities is measured; however, this ratio is also dependent on viscosity and temperature. Thus, pyrene is not truly a self-quenching fluorophore.

Finally, Nichols, J. W., *Seminars in Cell and Developmental Biology* (2002) 13:190-184 measured trafficking of phospholipids using N-nitrobenz-2-oxa-1,3-diazol-4-yl (NBD) as label. The paper does not concern an assay for levels of PLTP; rather, the movement of phospholipids in various contexts is measured.

Measurement of PLTP activity has been handicapped by an extremely high background of spontaneous transfer from donor to acceptor. In addition, many prior art assays are heterogeneous assays and thus require separation of donor from acceptor before measurement is made. The present invention minimizes the background of spontaneous transfer; in one embodiment, the assay is conducted as a homogeneous assay, thus offering added convenience.

DISCLOSURE OF THE INVENTION

The invention is directed to assays for PLTP activity which have improved signal-to-noise ratios. In one embodiment, the assays are homogeneous assays that permit fewer manipulations and ease of measurement.

Thus, in one aspect, the invention is directed to a method to determine the PLTP activity in a sample which method comprises incubating a reaction mixture containing said sample with donor particles comprising labeled PLTP substrate, which donor particles have aqueous cores and with an acceptor emulsion under conditions of osmotic pressure wherein said donor particle is disrupted and measuring the amount of label incorporated into said acceptor, thus determining the PLTP activity.

In one embodiment, the measuring of the amount of label incorporated into said acceptor is performed on the mixture itself, in a homogeneous assay.

In another aspect, the invention is directed to a kit for conducting the method which comprises a donor particle comprising a labeled PLTP substrate and aqueous core. The kit may also comprise an acceptor emulsion and a solute for enhancing osmotic pressure on the donor particle. The kit will include instructions for conducting the assay.

In other aspects, the invention is directed to screening for defects in the gene encoding PLTP, identifying compounds that modulate PLTP activity, assessing medical conditions correlated to PLTP activity including determining coronary disease risk. In all of these applications, the assay method of the invention is employed. For assessment of medical conditions or gene defects, the PLTP activity in a sample from a subject to be tested is compared to the activity of a sample derived from normal subjects. This value may be prerecorded. In identifying a compound which modulates the activity of this enzyme, the activity is compared in the presence and absence of the compound.

MODES OF CARRYING OUT THE INVENTION

Figure 1:
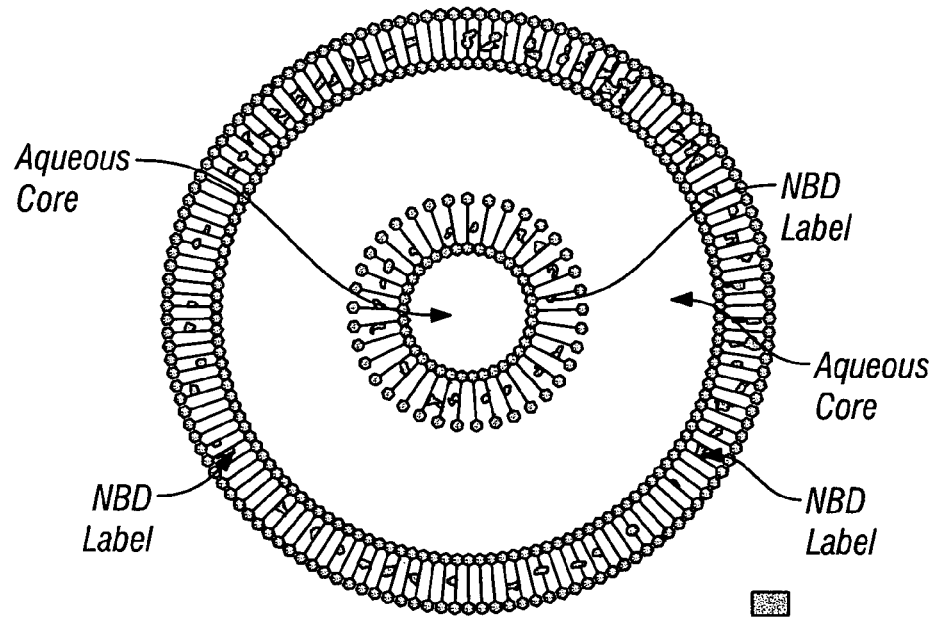
FIG. 1 shows a typical donor particle (a liposome) comprising substrate.

Abnormal PLTP activity has been associated with a number of conditions including hyperlipidemia, increased secretion in levels of Apo-B containing lipoproteins, and heart disease. Abnormal PLTP function can be readily addressed by dietary, pharmaceutical and exercise regimens. Thus, it is important to provide an assay for PLTP activity that is accurate and free of background levels that make interpretation of the results difficult or inaccurate.

The present invention provides an assay which results in a diminution of background readout in comparison to signal. The assay is based on the disruption of a donor particle containing an aqueous core by providing sufficient osmotic pressure to effect such disruption. By modifying the donor particle in this way, spontaneous transfer of the substrate to the acceptor is greatly reduced.

The participants in the assay are the labeled substrate, which represents the moiety to be transferred, a donor particle, which represents the original residence of the substrate, and an acceptor emulsion which is the moiety to which the substrate is transferred.

The substrate for PLTP will be a moiety that the enzyme is capable of transferring. Such moieties include phospholipids such as phosphatidylcholine (PC), phosphatidylethanolamine (PE), phosphatidylinositol (PI), and phosphatidylserine (PS) as well as diacylglycerols (DG), sphingomyelin (SM), lipopolysaccharides (LPS) and Vitamin E. Other potential substrates may be tested in the assay of the invention to ascertain their ability to be transferred by this enzyme.

The donor particle contains a lipid capsule which surrounds one or more aqueous cores. Such moieties are generally known as liposomes and may be unilamellar or multilamellar. It will be noted that the substrate itself may be a member of the hydrophobic layer which makes up the structure of the donor particle. Indeed, the donor particle may be composed entirely of substrates for the PLTP enzyme. The designation of one or another of the components as a substrate is accomplished through labeling.

Thus, the liposomes that behave as donor particles will typically comprise phospholipids such as the above-mentioned substrates but may also include other components such as neutral lipids such as triglycerides and cholesterol. The components of the liposomes may include positively charged lipids, negatively charged lipids and neutral lipids. The ratio of the components, is such that the component designated as a substrate is in excess, if a self-quenching fluorophore is used as label; otherwise the ratio may be more variable. Typically, the ratio of the substrate to additional components of the liposome is of the order of 5:1 to 2:1 in the case of self-quenching labels; other acceptable ratios may be found by routine optimization. Typical components of the liposomes which behave as donor particles include dipalmitoyl phosphatidylserine (DPPS), distearoyl phosphatidylserine (DSPS), dilauroyl phosphatidylserine (DOPS), dimyristyl phosphatidylserine (DMPS), and the corresponding phospholipids wherein the phosphate moiety is coupled to ethanol, choline, inositol, and the like. This list is merely illustrative and not inclusive.

The acceptor is typically an emulsion comprising particles which are lipid-based and lack an aqueous core or, theoretically, contain an aqueous core of high osmotic pressure. Typical emulsions contain, for example, high density lipoprotein particles or contain micelles formed from triglycerides. The acceptor emulsions may also contain proteins for stability. The characterizing feature of the acceptor, however, is that it is an emulsion wherein the emulsified lipids do not contain aqueous cores.

Preparation of the donor particles is accomplished using standard methods known in the art, such as those described in "Liposomes: Rational Design" (A. S. Janoff, ed., Marcel Dekker, Inc., NY) or by any alternative techniques generally known in the art. Typically, the lipophilic components are dissolved in an organic solvent and sonicated or microfluidized in aqueous buffer. As the substrate is a structural component of the liposome, it is unnecessary to invoke a specific procedure for encapsulation or to provide procedures for removal of unencapsulated material.

The acceptor composition is prepared as an emulsion with a preponderance of neutral lipids, and, preferably, includes some protein as a stabilizing agent. Alternative acceptors include lipoproteins (e.g., HDL, LDL, and VLDL) and a synthetic emulsion similar to lipoproteins comprising, for example, 0.25 mg cholesterol/ml of emulsion, 1 to 15 mg protein (casein or Apo-AI)/ml of emulsion, a phospholipid selected from phosphatidylcholine, phosphatidylethanolamine, phosphatidyl-L-serine, phosphatidylinositol, phosphatidic acid, phosphatidyl-DL-glycerol, lysophosphatidylcholine, sphingomyelin, and cardiolipin at 10 to 200 mg phospholipid/ml of emulsion, and triglyceride. These lipids may be present in mass at a range similar to that found in lipoproteins. These emulsions are prepared by sonication or microfluidization as well. Alternatively, commercially available suspensions such as milk or solid forms thereof may be used in suitable dilutions.

Typically, a solution with a concentration of solute effective to generate a desired osmolality is added to the acceptor emulsion prior to mixing with a suspension of the donor particles; however the solute solution may be added at the time of the assay.

The substrate contained in the donor particles comprises a label that will track the progress of the substrate from the donor particle to the acceptor. If the assay is performed in a heterogeneous format, virtually any label can be used since the acceptor and donor particle will ultimately be separated. For example, the acceptor itself might be coupled to a member of a specific binding pair such as an antibody or fragment thereof or biotin and removed from the reaction mixture at various times and the level of label assessed. Thus, in this instance, the substrate may be labeled with a radioisotope, a fluorescent moiety, an enzyme (which then can be assayed using standard enzyme-based assays) or any other suitable label known in the art. Thus, for example, the heterogeneous assays described in U.S. Pat. No. 5,610,019 can be adapted to the method of the invention by substituting for the labeled donor VLDL or LDL, the donor particles of the invention, and adjusting the osmotic pressure. In the assay described in the '019 patent, the acceptor is biotinylated HDL, and the substrate is tritiated phosphatidylcholine. The transfer of the tritiated substrate to acceptor which is separated using streptavidin coupled beads, is measured by scintillation counting. Performing such assays using the donor particles and osmotic pressures of the invention provides superior results due to lowering the level of spontaneous transfer.

However, in a preferred method, the assay is performed in a homogeneous format by taking advantage of the ability of a label to change its properties depending on its environment. A particularly preferred label is a self-quenching fluorescent molecule which, when removed from a concentrated environment exhibits enhanced fluorescence due to the lack of proximity of the fluorescent molecules. Alternatively, the intensity of fluorescence may simply change depending on the environment per se. It is known, for example, that rubidium complexes, p-azophenylarsonate, and fluorescein are quenched when bound to antibodies while antibodies raised against ε-dansyl lysine enhance the fluorescence of this compound when bound to the antibody. The acceptor emulsion, since it may contain proteins, may include antibodies which are specific for the label or substrate and thus affect the fluorescence properties of the label. Other examples of moieties whose signal is affected by the environment include clusters of metal atoms known as "quantum dots" whose fluorescence properties are a function of the environment in which they are found. See, for example, U.S. Pat. No. 6,207,392 incorporated herein by reference.

Other labels whose signals are affected by the environment include materials which exhibit nuclear magnetic resonance, where exposure to aqueous environments greatly affects with signal produced.

Thus, for use in a homogeneous assay, the label coupled to substrate will be such that its signal is altered when it passes from donor particle to the acceptor emulsion. Preferred are self-quenching fluorescent labels, such as dansyl, rhodamine, fluorescein, BODIPY, and the like.

A particularly preferred label is the fluorescent self-quenching moiety nitrobenz-2-oxa-1,3-diazol-4-yl (NBD) which can be readily coupled to phospholipids, such as phosphatidylethanolamine, to provide the substrate NBD-PE.

To conduct the assay, a suspension of the donor particles in buffer is contacted with the acceptor emulsion and with a solution of solute which provides an osmolality(measured in osmoles of solute per kilogram of solvent) which is equivalent to that provided by a solution containing sodium bromide at a density in the range of 1.05-1.15 g/ml. It appears that at this level of osmotic pressure, optimum results are obtained. Particularly preferred is an osmotic pressure equivalent to that exerted by a solution of sodium bromide at a density of 1.1 g/ml.

While the osmolality of the solution is described in terms of the density of sodium bromide solutions, any ionic salt may be used to generate similar osmotic pressures. Thus, potassium bromide, sodium chloride, sodium bromide, and other halides as well as soluble sulfates or phosphates could also be used. Sodium bromide and potassium bromide are preferred.

Thus, a solution of sodium chloride, sodium bromide, or other salts capable of conferring similar osmotic pressures is added to a reaction mixture of sample, donor particles and acceptor emulsion suspended in buffer at an amount sufficient to provide the requisite osmotic pressure; alternatively, the salt solution may be included in the acceptor composition. The donor particles and acceptor emulsion, all in buffer solution, are maintained at the appropriate osmotic pressure for sufficient time to effect transfer, typically about 5-30 minutes, preferably 8-20 minutes, at about 30-37° C. The transfer can be monitored by the transfer of label as described above at various times after mixing. The signal is monitored in a manner appropriate to the choice of label; in a preferred embodiment, the enhancement of fluorescence of a self-quenched label is measured in a homogeneous assay.

The transfer of label can be compared in the presence and absence of a compound which is a candidate for modulating the activity of PLTP; a diminution or enhancement of transfer in the presence as compared to the absence of such compound identifies it as a modulator. Similarly, a diminution or enhancement of PLTP activity in a test sample, as compared to a standard, indicates a discrepancy between the standard and the test sample. If the standard comprises activity present in biological samples from a normal subject or a population of subjects, the deviation in the test sample indicates an abnormality in the subject from which the sample is taken.

Figure 2:
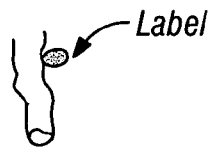
FIG. 2 shows a schematic representation of the PLTP assay.
Figure 2:
Figure 2:
Figure 2:
Figure 2:

The general principles of one embodiment of the assay are shown in FIGS. 1 and 2. FIG. 1 is simply a schematic of a liposome indicating that the substrate component of the lipid bilayer is associated with a label. FIG. 2 shows the transfer of the labeled substrate to the acceptor emulsion in the presence of PLTP. As seen, upon providing osmotic pressure to the buffer in which the donor particles and receptor reside, the labeled substrate is transferred in a reaction catalyzed by PLTP to the acceptor emulsion which results in enhancement of fluorescence.

The components useful in the invention can be provided in the form of a kit which contains at least a container which provides labeled donor particles either suspended in buffer or lyophilized and, optionally, a container which contains a buffer solution of acceptor at a tonicity which will provide the appropriate osmolality when mixed with the donor particles in the reaction mixture. Also included is a set of instructions for conducting the assay. If desired, only the container of labeled donor particles may be provided, along with instructions for the preparation of the acceptor emulsion and the osmotic pressure-conferring material. As the acceptor suspension may be prepared from simple materials, such as milk, and as the salts for obtaining the suitable osmotic pressure are readily available, it may be adequate to provide the user simply with instructions for addition of these components.

Applications

The assay of the present invention may be used to assess a medical condition; these conditions include but are not limited to hyperlipidemia, increased secretion and levels of ApoB-containing lipoproteins, and risk factors for coronary disease. These conditions may be treated with agents affecting PLTP activity.

The assay is performed on a biological fluid derived from a test subject. As used herein, "biological fluid" refers to fluids derived from a subject which are expected to contain PLTP, or are fluids which are extracts from biopsied organs which may be expected to contain PLTP. Most conveniently, the assays are performed on plasma or serum. However, other biological fluids may be used, depending on the interest of the experimenter. Any vertebrate subject of interest may be used as a source of biological fluid; most commonly, the assays will be performed on human samples; however, the assay is also useful in determining these levels in other animals such as livestock, companion animals, zoo animals, and other species subject to veterinary care.

As an example, a dietary modification regimen may be prescribed by a health care professional that directly affects the induction, activity, transcription or translation of PLTP. A baseline PLTP value is determined for a subject using the methods and kits described herein; this is compared to a pre-determined range of values considered normal for the subject's species, phenotype, age, gender, and/or genotype. Where the subject's PLTP value is outside the norm, a treatment affecting PLTP activity is recommended, which may comprise dietary modification regimen, a compound that modulates PLTP activity, a compound that affects the transcription/translation of the PLTP gene, an exercise regimen, or combination thereof. The treatment is monitored by assessing the PLTP values in the subject over time. The treatment may be altered according to these results.

Thus, the application of the assay method during a course of treatment of a subject evaluates the ability of the treatment to control the levels and/or activity of PLTP in the subject. The treatment may be effective through inhibition or enhancement of the activity of PLTP, or by inhibition or enhancement of the production of this enzyme. If the latter, the treatment may operate through controlling transcription of the gene encoding this protein or translation of the resulting RNA or both.

The ability of a compound or protocol to modulate the activity of PLTP may also be determined in vitro by conducting the assay in the presence and absence of this compound as described above. The effect of the compound on the activity of a known level of PLTP will identify it as an inhibitor or enhancer of activity.

The following examples are offered to illustrate but not to limit the invention.

EXAMPLE 1

Determination of PLTP in Standard Samples

The donor particles are comprised of phosphatidylcholine (PC) and labeled phosphatidylethanolamine (PE) coupled to NBD. The ratio of labeled substrate NBD-PE to the remainder of the structural phospholipid, PC, must be >50% to permit sufficient self-quenching.

Two compositions of donor particles were prepared:

Composition A: 10.458 mmoles NBD-PE+4.482 mmoles of PC; or

Composition B: 10.458 mmoles NBD-PE+2.6145 mmoles PC.

Mixtures containing Composition A or Composition B dissolved in chloroform were dried under argon. Traces of solvent were removed under vacuum. To the vessels containing each composition were added 10 ml buffer solution (10 mM Trizma/150 mM saline/pH 7.4+1 mM EDTA). The mixtures were sonicated for 30 minutes at 30° C. and centrifuged to remove any particulates, and the suspended donor particles stored at 4° or 25° C. In the assays below, the donor particles derived from composition B were used.

In a first assay, the acceptor emulsion comprises high density lipoprotein (HDL) dialyzed to 1.006 g/ml and mixed 1:1 with 1.4 g/ml NaBr.

The reaction mixture contains 50 µl acceptor emulsion; 2.5 µl of the donor particle preparation, 42.5 µl of assay buffer (10 mM Trizma/150 mM NaCl/1 mM EDTA) and 5 µl of test solution containing blank, inactivated PLTP, or 2.5 µg/ml PLTP. Inactivated PLTP was prepared by incubating with one-fifth volume of antiserum or saline at 37° C. for fifteen minutes.

The assay mixture was incubated at 30° C. and fluorescence is read at times 0, 8 minutes and 16 minutes using an excitation wavelength of 465 nm and an emission wavelength of 535 nm. The results, recorded in fluorescence intensity units (FIU) as an average of three independent determinations, are shown in Table 1.

TABLE 1

| Time | Blank | Inactivated PLTP | PLTP |
|------|-------|------------------|------|
| 0    | 364   | 416              | 360  |
| 8    | 627   | 648              | 3532 |
| 16   | 795   | 815              | 4527 |

As seen, the blank shows minimal transfer over a 16 minute interval. Similarly, little transfer is effected in the assay containing inactivated PLTP. However, the inclusion of PLTP results in a dramatic increase in fluorescence intensity.

A second assay was performed using, as an acceptor, a mixture which is defined herein as a triglyceride emulsion (TGE). This acceptor comprises a 1:1 mixture with 1.4 g/ml NaBr of a sonicated emulsion which contains a concentration of 25 mg cholesterol/dL of emulsion; 500 mg casein/dL of emulsion; 140 mg phospholipid/dL of emulsion; and 700 mg triglyceride/dL of emulsion.

The assay was performed as described above with respect to the HDL acceptor and the results are shown in Table 2 as fluorescence intensity units after 25 minutes of incubation at 30° C. The results of an assay run concomitantly in exactly the same manner but using HDL as an acceptor are shown in Table 3. As indicated, although the blanks in both assays showed comparable values after 25 minutes of incubation, the levels of PLTP activities were approximately two-fold higher when the triglyceride emulsion was used as acceptor. Thus, the signal to noise ratio is enhanced by approximately a factor of 2 by using the TGE acceptor.

TABLE 2

| (TGE) | | | |
|---|---|---|---|
| Time | Blank | Inactivated PLTP | PLTP |
| 0  | 978  | 887  | 958   |
| 25 | 1283 | 1172 | 11682 |

TABLE 3

| (HDL) | | | |
|---|---|---|---|
| Time | Blank | Inactivated PLTP | PLTP |
| 0  | 835  | 796  | 877  |
| 25 | 1157 | 1247 | 5937 |

EXAMPLE 2

Determination of a Standard Curve

A standard curve was generated using serial dilutions of the donor particle preparation prepared by dispersing 5 µl of the NBD-PE donor particle preparation (1 mM NBD-PE) in 2 ml of 100% isopropyl alcohol and serially diluting this dispersion in IPA. The fluorescence intensity (465 nm excitation, 535 nm emission) of the diluted samples was read, with the results shown Table 4. Thus, a standard curve was created in the range from 0 pmoles of NBD-PE to 500 pmoles.

TABLE 4

| FIU | | average FIU | NBD-PE pm |
|---|---|---|---|
| 30690 | 29376 | 30033 | 500 |
| 15417 | 14894 | 15155 | 250 |
| 7998  | 7998  | 7998  | 125 |
| 4246  | 4207  | 4226  | 62.5 |
| 2228  | 2228  | 2228  | 31.25 |
| 1199  | 1245  | 1222  | 15.63 |
| 644   | 667   | 655   | 7.8 |
| 82    | 79    | 80    | 0 |

The fluorescence intensity (Y) is plotted against picomoles (X) to obtain a standard curve. Regression analysis indicates high correlation to a straight-line relationship between concentration of NBD-PE and fluorescence intensity units. A Y-intercept and slope for the standard curve are calculated, thus permitting a calculation of total numbers of picomoles transferred from FIU. Analysis of the statistical data give a Y-intercept of 312.9 and a slope of 59.6.

EXAMPLE 3

Application of Standard Curve to Experimental Data

Figure 3:
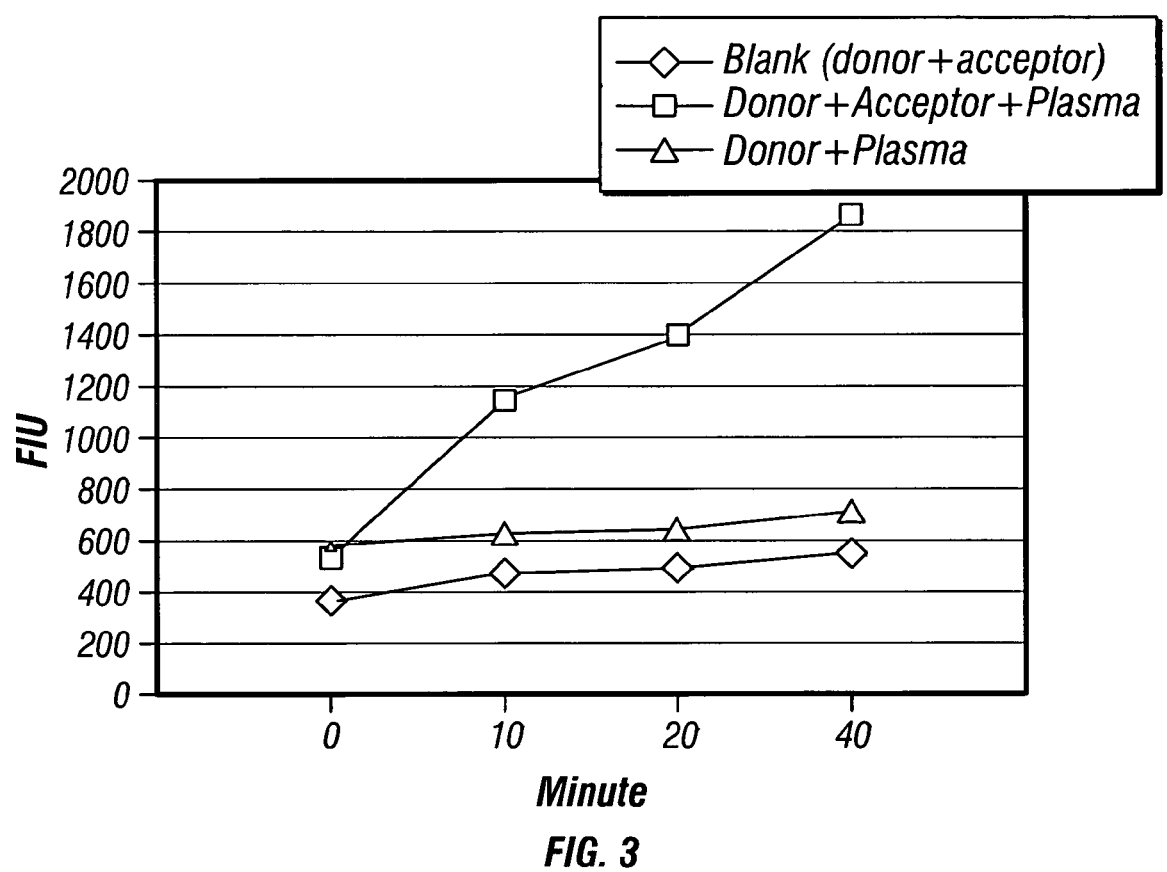
FIG. 3 is a graph showing the time course of substrate transfer using plasma as a source of PLTP. Plasma PLTP activity is shown at d=1.1 gm/ml.

The assay was performed as described in Example 1 using TGE acceptor and a 3 µl plasma sample as the source of PLTP activity. The results are shown in FIG. 3.

Applying the standard curve of Example 2 to these results, a value representing the picomoles of NBD-PE transferred in the sample can be calculated. At the 40 minute time point, the FIU reading is approximately 1900; the average blank reading is approximately 600, thus providing an FIU of value due to the catalyzed transfer of approximately 1300. Applying the linear equation, a value of approximately 17 picomoles transferred by 3 µl plasma in 40 minutes is obtained.

EXAMPLE 4

Determination of Optimum Osmolality

Figure 4:
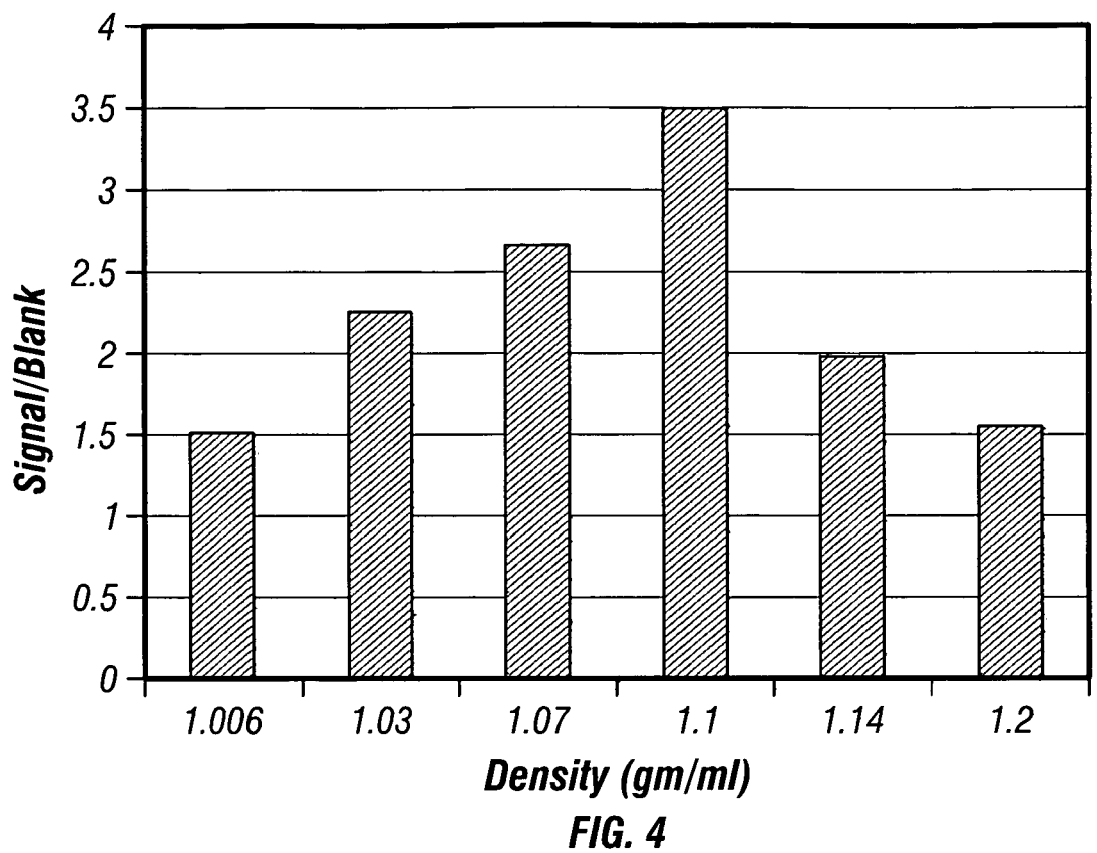
FIG. 4 is a graph indicating the ratio of fluorescence units observed in the presence of PLTP as compared to its absence as a function of the osmotic pressure of the reaction mixture.
Figure 5:
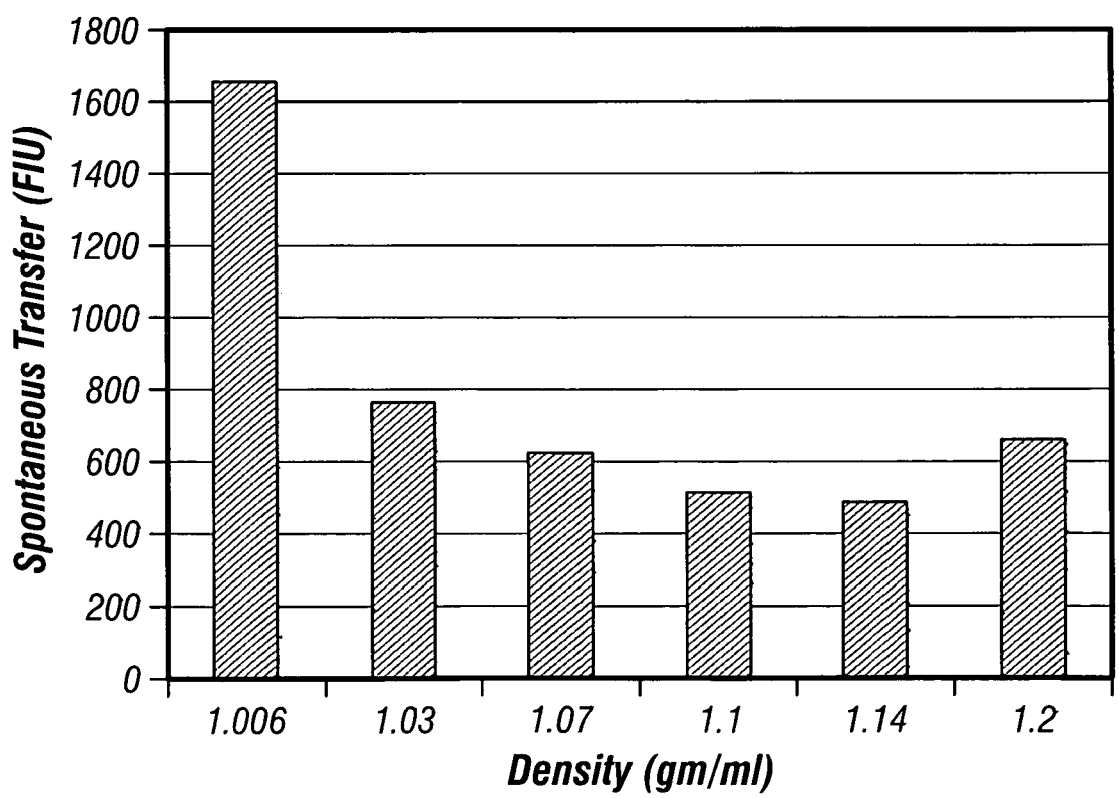
FIG. 5 is a graph showing the fluorescence units generated by spontaneous transfer of substrate to acceptor as a function of osmotic pressure.

The assay was performed as described in Example 1 using TGE acceptor but varying the concentration of NaBr to result in densities of the reaction mixture ranging from 1.006 g/ml to 1.2 g/ml. The results are shown in FIG. 4 as the ratio of the signal generated by the PLTP containing sample to the fluorescence generated by the blank. As shown, the highest ratio, 3.5, occurs at a density of 1.1 g/ml reaction mixture.

In addition, these results were plotted in terms of the level of spontaneous transfer as measured by fluorescence units at these salt concentrations. As shown, the spontaneous transfer is minimized at density levels of 1.1-1.14 g/ml reaction mixture.

As is understood, the osmolality generated by a given density of salt concentration is dependent on the nature of the salt. The corresponding concentrations of other salts, such as $MgCl_2$, NaCl, and the like, can be calculated accordingly.

The invention claimed is:

1. A method to determine the activity of phospholipid transfer protein (PLTP) in a sample, which method comprises,
   (a) providing an initial reaction mixture, maintained in a buffer, wherein the initial reaction mixture has a physiological salt concentration having a density of about 1.006 g/ml, and the initial reaction mixture comprises:
      (i) the sample comprising PLTP, and
      (ii) a donor particle comprising a labeled PLTP substrate and an aqueous core;
   (b) adding an acceptor emulsion to the initial reaction mixture, wherein the acceptor emulsion comprises an acceptor to which the substrate may be transferred;
   (c) adding a salt solution to the initial reaction mixture making the initial reaction mixture a final reaction mixture, wherein the salt solution added has a density greater than about 1.006 g/ml, and wherein the density of the final reaction mixture is greater than about 1.006 and less than about 1.2 g/ml, and
   wherein addition of the salt solution to the initial reaction mixture causes the donor particle comprising the labeled PLTP substrate to be disrupted, allowing PLTP to transfer the labeled PLTP substrate to the acceptor; and
   (d) measuring the amount of labeled PLTP substrate transferred to the acceptor, thus determining the PLTP activity of the sample.

2. A method to determine the activity of phospholipid transfer protein (PLTP) in a sample, which method comprises
   (a) providing an initial reaction mixture, maintained in a buffer, wherein the initial reaction mixture has a physiological salt concentration having a density of about 1.006 g/ml, and the initial reaction mixture comprises:
      (i) the sample comprising PLTP,
      (ii) a donor particle comprising a labeled PLTP substrate and an aqueous core, and
      (iii) an acceptor emulsion comprising an acceptor to which the substrate may be transferred;
   (b) adding a salt solution to the initial reaction mixture making the initial reaction mixture a final reaction mixture, wherein the salt solution added has a density greater than about 1.006 g/ml, and wherein the density of the final reaction mixture is greater than about 1.006 and less than about 1.2 g/ml, and wherein addition of the salt solution to the initial reaction mixture causes the donor particle comprising the labeled PLTP substrate to be disrupted, allowing PLTP to transfer the labeled PLTP substrate to the acceptor; and
   (c) measuring the amount of labeled PLTP substrate transferred to the acceptor, thus determining the PLTP activity of the sample.

3. The method of claim 1 or 2, wherein measuring the amount of labeled PLTP substrate transferred to the acceptor comprises performing the measuring step on the final reaction mixture without separating the acceptor from the final reaction mixture.

4. The method of claim 3, wherein the label is a self-quenching fluorescent molecule.

5. The method of claim 4, wherein the label is N-(7-nitrobenz-2-oxa-1,3-diazol-4-yl) (NBD), fluorescein, dansyl, boron dipyrromethane difluoride, or rhodamine, or derivatives thereof.

6. The method of claim 5, wherein the label is NBD.

7. The method of claim 1 or 2, wherein the acceptor emulsion comprises high density lipoprotein (HDL) or comprises triglycerides.

8. The method of claim 7, wherein the acceptor emulsion comprises cholesterol, protein, phospholipid and triglyceride.

9. The method of claim 1 or 2, wherein the salt solution is a sodium bromide (NaBr) solution.

10. The method of claim 1 or 2, wherein the density of the final reaction mixture reaches about 1.1 g/ml.

11. The method of claim 1 or 2, which further comprises comparing the amount of labeled PLTP substrate transferred to the acceptor with a standard in which an amount of labeled PLTP substrate is transferred to the acceptor by a known concentration of PLTP.

12. The method of claim 11, which further comprises computing, from the standard, the amount of labeled PLTP substrate transferred.

13. A method to identify a compound which modulates the activity of PLTP, which method comprises
   a) performing the method of claim 1 or 2; and
   b) performing the method wherein the reaction mixture further comprises a test compound;
   c) comparing the activity of PLTP determined in the method of step a) and step b), wherein a difference in the activity identifies the compound as a modulator of PLTP activity.

14. A method to determine the presence of a condition in a test subject which condition is characterized by abnormal levels of PLTP activity, which method comprises performing the method of claim 1 or 2 using a biological fluid from the test subject as the sample to determine the level of PLTP activity in the sample; and comparing the level obtained from the method to the level of PLTP activity characteristic of a normal subject;

whereby a difference in the level of PLTP activity in the test subject as compared to the normal subject indicates a condition characterized by abnormal PLTP activity levels in the test subject.

15. The method of claim 1 or 2, wherein the salt in the salt solution is selected from the group consisting of potassium halide, potassium sulfate, potassium phosphate, sodium halide, sodium sulfate, sodium phosphate, potassium bromide, sodium chloride, sodium bromide, and magnesium chloride.

16. The method of claim 15 wherein the salt is sodium bromide or potassium bromide.

17. The method of claim 1 or 2, wherein the salt solution is an ionic salt solution.

18. The method of claim 1 or 2, wherein the salt solution comprises a halide, a soluble sulfate, or a soluble phosphate.

19. The method of claim 1 or 2, wherein the sample is a biological fluid.

20. The method of claim 19, wherein the biological fluid is plasma or serum.

21. A method to determine the activity of phospholipid transfer protein (PLTP) in a sample, which method comprises, (a) providing a initial reaction mixture, maintained in a buffer, wherein the initial reaction mixture comprises about a 1:1 ratio of an acceptor emulsion at a density of about 1.006 g/ml, and a NaBr salt solution at a density of about 1.4 g/ml, wherein the acceptor emulsion comprises an acceptor to which a substrate may be transferred;

(b) adding to the initial reaction mixture:
        (i) the sample comprising PLTP, and
        (ii) a donor particle comprising a labeled PLTP substrate and an aqueous core, making the initial reaction mixture a final reaction mixture;

wherein the NaBr salt solution raises the density of the final reaction mixture to about 1.1 g/ml, and wherein the change in density of the initial reaction mixture and the final reaction mixture causes the donor particle comprising the labeled PLTP substrate to be disrupted, allowing PLTP to transfer the labeled PLTP substrate to the acceptor; and (d) measuring the amount of labeled PLTP substrate transferred to the acceptor, thus determining the PLTP activity of the sample.

\* \* \* \* \*